United States Patent [19]
Jamas et al.

[11] Patent Number: 5,504,079
[45] Date of Patent: Apr. 2, 1996

[54] **METHOD FOR IMMUNE SYSTEM ACTIVATION BY ADMINISTRATION OF A β(1-3) GLUCAN WHICH IS PRODUCED BY *SACCHAROMYCES CEREVISIAE* STRAIN R4**

[75] Inventors: Spiros Jamas, Boston; D. Davidson Easson, Jr., Shrewsbury; Gary R. Ostroff, Worcester, all of Mass.

[73] Assignee: Alpha-Beta Technology, Inc., Worcester, Mass.

[21] Appl. No.: 339,632

[22] Filed: Nov. 14, 1994

Related U.S. Application Data

[63] Continuation of Ser. No. 109,412, Aug. 19, 1993, abandoned, which is a continuation of Ser. No. 977,740, Nov. 16, 1992, abandoned, which is a continuation of Ser. No. 404,765, Sep. 8, 1989, abandoned.

[51] Int. Cl.$^6$ .................................................. A61K 31/715
[52] U.S. Cl. .......................... 514/54; 536/1.11; 536/114; 536/123.12
[58] Field of Search ....................... 536/1.1, 114; 514/54

[56] References Cited

U.S. PATENT DOCUMENTS

| | | | |
|---|---|---|---|
| 4,343,784 | 8/1982 | Massot et al. | 424/45 |
| 4,739,046 | 4/1988 | DiLuzio | 435/101 |
| 4,761,402 | 8/1988 | Williams et al. | 536/1.1 |
| 4,810,646 | 3/1989 | Jamas et al. | 514/54 |

OTHER PUBLICATIONS

Ostroff et al., "Manipulation of Yeast Glucan Structure: Molecular Weight, Branch Frequency and Branch Length", *The Fermentor*, 9(12):51, American Chemical Society, Abstract No. 19, (Aug. 1989).

J. K. Czop, *Pathology and Immunopathology Research*, 5:286–296 (1986).

N. R. DiLuzio et al., *International Journal of Cancer*, 24:773–779 (1979).

J. A. Cook et al., *Survey of Immunological Research*, 2:243–245 (1983).

W. Browder, *Survey of Immunological Research*, 2:299–301 (1983).

M. L. Patchen, *Survey of Immunological Research*, 2:237–242 (1983).

J. A. Cook et al., *Infection and Immunity*, 37(3):1261–1269 (1982).

T. W. Holbrook et al., *American Journal of Tropical Medical Hygiene*, 32(1):51–53 (1983).

T. W. Holbrook et al., *American Journal of Tropical Medical Hygiene*, 30(4):762–768 (1981).

J. A. Cook et al., *Infection and Immunity*, 40(3):1038–1043 (1983).

M. A. Chirigos et al., *Cancer Research*, 38:1085–1091 (1978).

J. A. Reynolds et al., *Infection and Immunity*, 20(1):51–57 (1980).

J. L. Benach et al., *Infection and Immunity*, 35(3):947–951 (1982).

E. R. Sherwood et al., *International Journal of Immunopharmacology*, 9(3):261–267 (1987).

International Search Report.

*Primary Examiner*—Marian C. Knode
*Assistant Examiner*—Jean C. Witz
*Attorney, Agent, or Firm*—Hamilton, Brook, Smith & Reynolds

[57] ABSTRACT

Modified yeast cell wall glucans are administered to patients who are at risk for infection due to imminent surgery, chemotherapy or other treatment which affects the immune system, in order to mobilize the cellular defense mechanisms and boost the immune response of the patient before, during and after the surgery, chemotherapy or other treatment.

6 Claims, 14 Drawing Sheets

METHOD FOR IMMUNE SYSTEM ACTIVATION BY ADMINISTRATION OF A β (1-3) GLUCAN WHICH IS PRODUCED BY *SACCHAROMYCES CEREVISIAE* STRAIN R4

This is a continuation of application Ser. No. 08/109,412, filed on Aug. 19, 1993 (now abandoned), which is a continuation of Ser. No. 07/977,740, filed on Nov. 16, 1992, (now abandoned), which is a continuation of Ser. No. 07/404,765, filed Sep. 8, 1989, (now abandoned).

BACKGROUND

The metabolic responses to injury, infection and inflammatory diseases are composed of a variety of physiologic changes which are thought to limit the extent and magnitude of the injury or infection and promote wound healing. J. J. Pomposelli et al., *J. of Parenteral and Enteral Nutrition,* 12(2):212–218 (1988). The metabolic responses are characterized by a generalized and stereotypical pattern of reactions with limited specificity related to the etiology of the initiating event or to the organism. The physiologic changes observed during this response include an increased mobilization of amino acids from peripheral tissues, with a subsequent increase in the synthesis of hepatic proteins, a prominent leukocytosis with neutrophilia in the blood, as well as a redistribution in plasma trace metals. Some endocrinologic changes include a rise in plasma insulin, glucagon, and glucocorticoids. Fever, and a negative nitrogen balance are also indicative of the metabolic response to injury and infection. J. J. Pomposelli et al., *J. of Parenteral and Enteral Nutrition,* 12(2):212–218 (1988).

The metabolic response is orchestrated by cell mediators. A few of these cell mediators include interleukin-1 alpha and beta (IL-1), tumor necrosis factor alpha/cachetin (TNF), tumor necrosis factor beta/lymphotoxin, colony stimulating factor (CSF), platelet-derived growth factor (PDGF) and gamma interferon. These mediators, or monokines, are secreted by cells known as mononuclear phagocytes, in response to injury or infection of the host.

The primary immunologic mediator involved in the cellular defense mechanism is the lymphokine interleukin-1 (IL-1), which is synthesized by mononuclear phagocytes. Numerous studies have been carried out on the application of IL-1 to enhance non-specific resistance to infection in a variety of clinical states. Pomposelli et al., *J. Parent. Ent. Nutr.,* 12(2):212–218, (1988). The major problem associated with the use of IL-1 and other cellular mediators in humans is toxicity and side effects resulting from the disruption of the gentle balance of the immuno-regulatory network. Fauci et al., *Anals. of Internal Medicine,* 106:421–433 (1987). Therefore, it may be more reasonable, physiologic and effective to mimic the endogenous response of monokines by stimulation of their release rather than their exogenous administration.

Immunocompromised individuals e.g., chemotherapy or radiation therapy patients, patients having a immuno-depressing disease or disorder such as AIDS, or the over-65 age group, comprise a large group of patients who are at a high risk of post-operative or other complications. These complications are mainly due to secondary infections resulting from the treatment or surgical procedure and have severe implications in terms of patient morbidity and mortality.

Protein malnourished, injured and immunocompromised individuals have a substantially diminished capacity to produce the necessary metabolic responses to infection or injury which, in well nourished or immune-normal patients, enhance the body's ability to assemble humoral and cellular defense mechanisms involving leukocytes. In fact, protein malnutrition has been directly associated to an increased occurence and severity of bacterial infections. Moldawer et al., *J. Theor. Biol.,* 106:119–133 (1984).

Recent interest has focused on the treatment or prevention of disease by stimulating the production of immunologic cell mediators with microbial or plant-derived substances. For example, yeast cell wall glucans have an ability to stimulate certain aspects of the immune sysetm in mammals. The mechanism for this effect has been characterized, and involves a specific glucan receptor which is present on peripheral blood leukocytes and extravascular macrophages. Czop, J. K., *Path. Immunopath. Res.,* 5:286–296, (1986). Activation of this receptor with glucans stimulates the amplification of host defenses which involves a cascade of interactions primarily mediated by macrophages and macrophage-derived products, thereby increasing a patient's resistance to infection.

The cell walls of yeast organisms are mainly composed of β-linked glucan, a polysaccharide comprised of a backbone chain of β(1–3) glucose units with a low degree of inter- and intra- molecular branching through β(1–6) linkages. A minor component that consists mainly of highly branched β(1–6) glucan is closely associated with the main component, and both together comprise the alkali-insoluble glucan fraction.

The structure and/or preparation of β-glucans has been described by Manners et al., *Biochem J.,* 135:31–36 (1973), Sietsma et al., *J. of General Microbiology,* 114:99–108 (1979), Kopecka et al., *J. of Cell Biology,* 62:66–76 (1974), Kreger et al., *J. of General Microbiology,* 92:202–220 (1975) and DiLuzio et al. *Int. J. of Cancer,* 24:773–779 (1979). Use of a phosphorylated glucan for therapeutic purposes has been described by DiLuzio in U.S. Pat. No. 4,739,046 and by Williams et al. in U.S. Pat. No. 4,761,402.

SUMMARY OF THE INVENTION

The invention relates to a method of stimulating an immune response in a subject utilizing a class of modified yeast glucans which have significantly enhanced immunobiologic activity when compared to previously reported glucans, including naturally-occuring and existing commercial glucan preparations. The modified yeast glucan preparations which contain increased ratios of β(1–6): β(1–3) glycosidic linkages with respect to naturally occurring materials and have enhanced in vitro and in vivo macrophage activating properties. The method is particulary effective for potentiating an immune response in individuals (animals or humans) who are immunocompromised, or who are at risk of infection due to disease, hospitalization, age or other B predisposing medical factors. The method of the invention involves administering the modified glucans to an individual in an amount sufficient to potentiate the individual's immune response and trigger the series of events necessary to improve the individual's host defenses.

The modified glucans used in the present method are modified yeast-derived carbohydrate polymers having a higher ratio of β(1–6)/β(1–3) linkages than naturally-occurring (unmodified) glucans. Glucans used in the present method are modified by treating them, or the organism which produces them (e.g., yeast cells), to increase the ratio of β(1–6)/β(1–3) linkages in the structure. The modified β-glucans are structurally and functionally distinct from naturally-occurring, bacterial, plant and fungal glucans reported to date, or wild-type, yeast cell wall preparations, such as Zymosan (Sigma Chemical Co., St. Louis, Mo.) and Glucan-P (Accurate Chemical and Scientific Corp., Westbury, Conn.), in that the primary structure of the modified glucan has a higher degree of branching (i.e., more β(1–6) linkages) than wild-type preparations. This higher level of branching confers on the modified glucans a more extended conformation and increased solubility in aqueous media. For example, an aqueous solution of the modified glucan has a greater hydrodynamic volume than the wild-type glucano The most significant impact of the altered structure and conformation of the modified glucan is the ability to bind and activate the β-glucan receptors of monocyte macrophages with an affinity about 15 times greater than wild-type glucan preparations, as measured by competitive inhibition of Zymosan phagocytosis.

Modified glucan is a natural product, which has not been derivatized or chemically altered. That is, it does not contain any functional groups which are not present on naturally-occurring glucan. Thus, the present method utilizing the modified glucan preparation provides a safe effective method for administration to humans and animals to enhance resistance to microbial invasion and infection.

DETAILED DESCRIPTION OF THE INVENTION

The modified β-glucans useful in the present method are β-glucans having a higher ratio of β(1–6)/β(1–3) linkages with respect to naturally-occurring, wild-type glucan derived from bacteria, plants and fungi. The glucans of the present invention (hereinafter referred to as "modified β-glucans" or "modified glucans") have increased macrophage-activating properties over naturally-occuring glucans and therefore provide more potent activation of the immune response. Modified β-glucans are derived from the cell walls of glucan-containing cells, such as yeast cells, which have been treated to increase the degree of β(1–6) branching present in the glucan structure.

Glucan polymers with immunomodulating properties all share a common β(1–3)-linked linear glucose backbone. Many species, such as lentinan and scleroglucan, also contain periodic branching off the C-6 carbon atom of glucose units in the backbone. Table 1 lists a number of glucans with immunomodulatory properties and their general linkage structure as reported.

TABLE 1

| Glucans with Immunologic Activity | | |
|---|---|---|
| Glucan | Source | Linkages |
| Curdlan | *Alcaligenes faecalis* | β(1–3) |
| Soluble Phosphorylated Glucan | *Saccharomyces cerevisiae Coriolus versicolor* | β(1–3) |
| Aminated Glucan | fungi, bacteria, lichens | β(1–3) |
| Alkali-Insoluble Yeast Glucan | *Saccharomyces cerevisiae* | β(1–3)/β(1–6) |
| Lentinan | *Lentinus edodes* | β(1–3)/β(1–6) |
| Scleroglucan | *Sclerotium glucanicum* | β(1–3)/β(1–6) |
|  | *Sclerotium rolfsii* | β(1–3)/β(1–6) |
| Schizophyllan | *Schizophyllan commune* | β(1–3)/β(1–6) |

Figure 1:
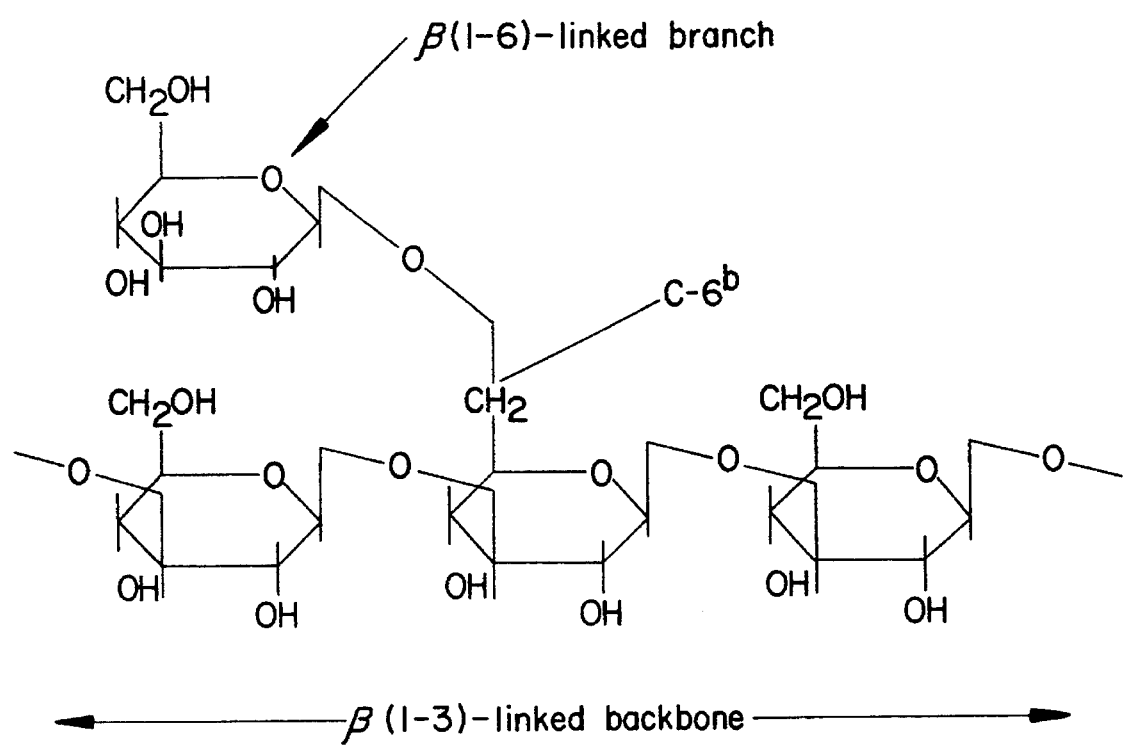
FIG. 1 is a schematic illustration of the common repeating unit in a glucan polymer showing the β(1–3)-linked backbone with a single β(1–6)-linked branch molecule.

Regardless of the source (e.g., organism) of the material, all the branched glucans listed in Table 1 contain a single glucose unit at the branch linked through a β(1–6) linkage to the backbone chain, as shown in FIG. 1.

Figure 2:
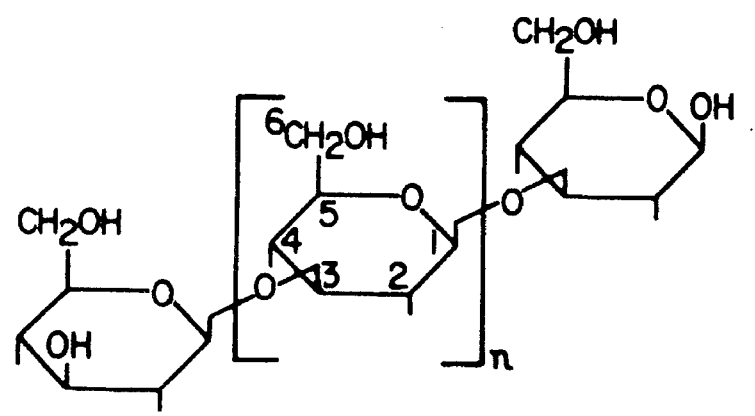
FIG. 2 is a $^{13}$C-NMR spectrum of a linear β(1–3)-linked glucan.
Figure 2:
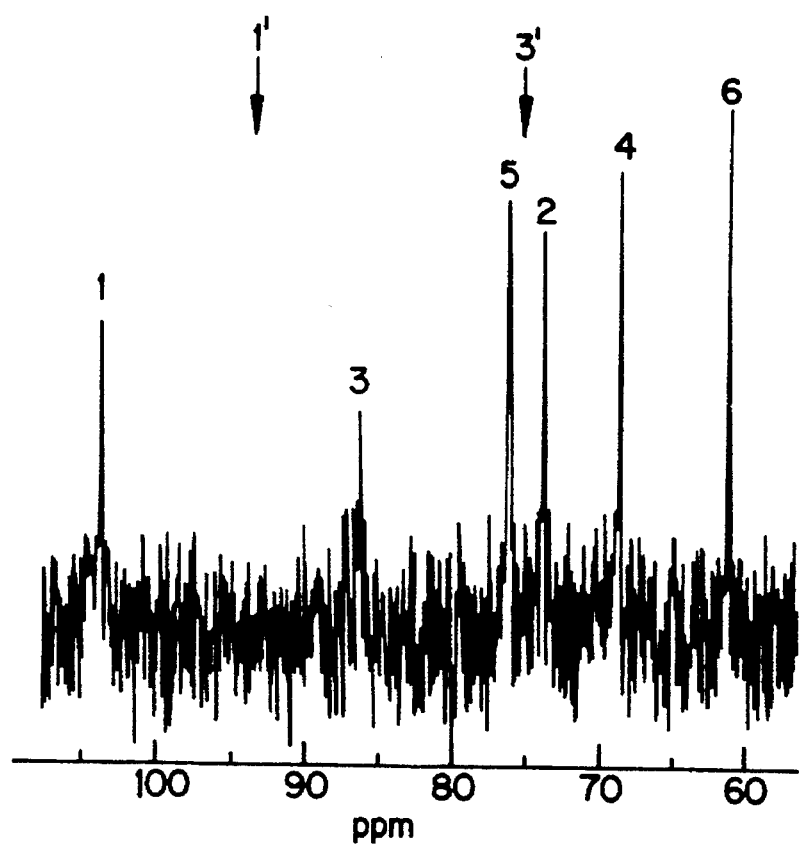

A common technique in determining linkage type and structure in glucans is carbon-13 nuclear magnetic resonance spectroscopy ($^{13}$C-NMR). The number and relative intensities of $^{13}$C signals in a given spectrum can be used to determine linkage configurations and positions in glucan polymers. For example, the chemical shifts (signals) of carbon atoms engaged in the glycosidic bond are shifted strongly downfield (up to 9 ppm) compared to the corresponding unlinked carbons. FIG. 2 demonstrates this phenomenon as observed for a linear β(1–3) linked glucan polymer. The spectrum shows the six signals obtained from the six carbon-atoms of the β(1–3) linked glucose units. The arrows (1'and 3') indicate the position of the C-1 and C-3 signals for D-glucose, demonstrating the shift which occurs for carbon atoms C-1 and C-3 which are engaged in the β(1–3) glycosidic linkage. Extensive NMR studies have been conducted with the glucans listed in Table 1 making this a useful technique in comparing their structures.

Figure 3:
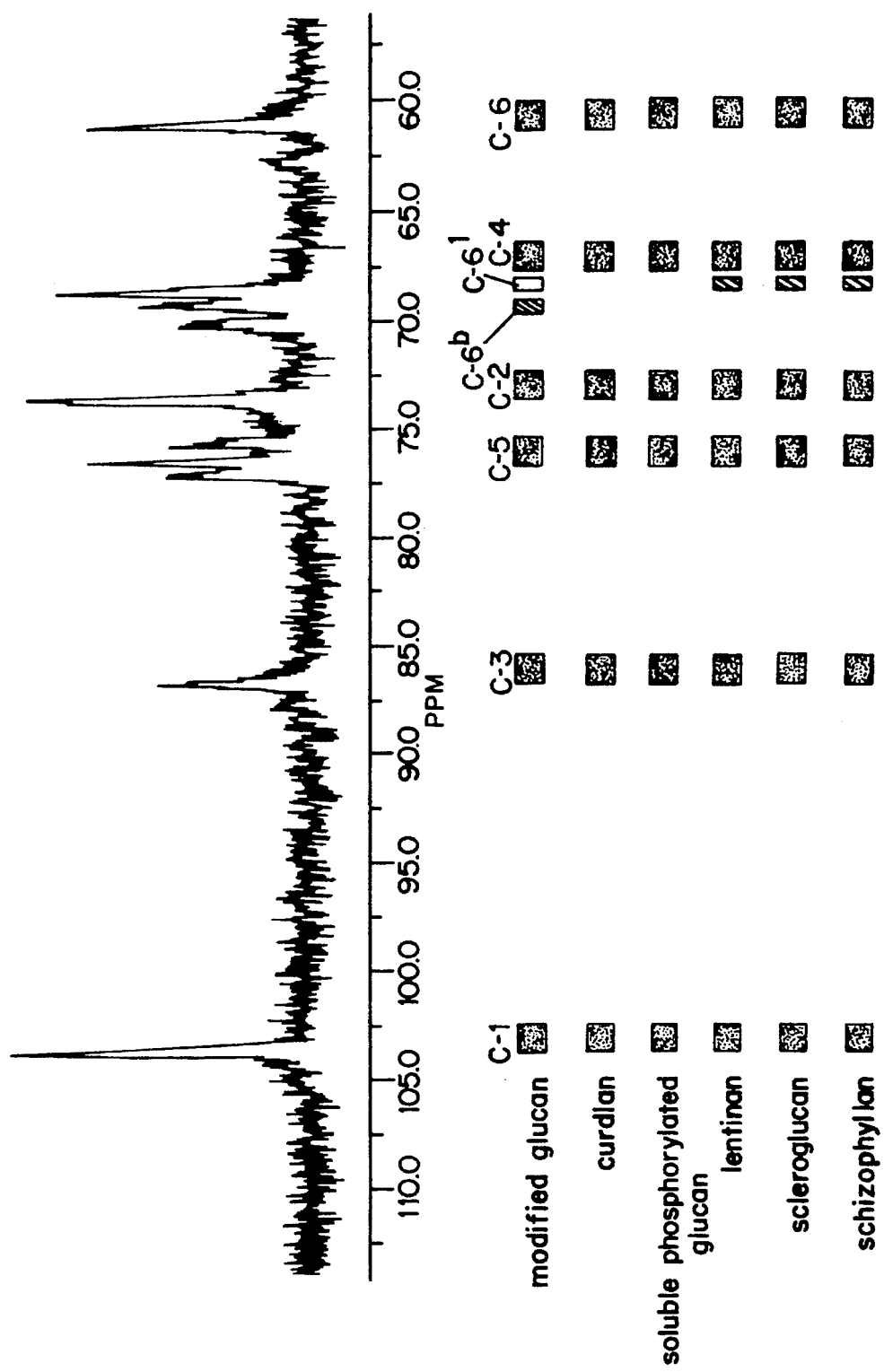
FIG. 3 is a $^{13}$C-NMR spectrum of a soluble modified glucan compared to the $^{13}$C-NMR spectra of naturally-occurring linear and branched glucans.

The distinction in the structure of the modified glucans can be clearly demonstrated in their $^{13}$C-NMR spectra. FIG. 3 illustrates a $^{13}$C-NMR spectrum of a "modified" glucan and summarizes the position of the $^{13}$C signals reported for previously reported glucans with immunologic activity (see Table 1). All the glucans listed in Table 1 share the six carbon signals of the β(1–3)-linked glucose moieties. Secondly, all previously reported branched glucans (e.g., Lentinan, Scleroglucan, Schizophyllan) give a characteristic signal at approximately 70 ppm shown as the shaded box in FIG. 3. This signal represents the C-6 atom at the branch point (3,6-di-O-substituted C-6) shown as C-$6^b$ in FIG. 1 which is displaced relative to the C-6 signal at 61 ppm due to its involvement in a β(1–6) glycosidic linkage.

Figure 4:
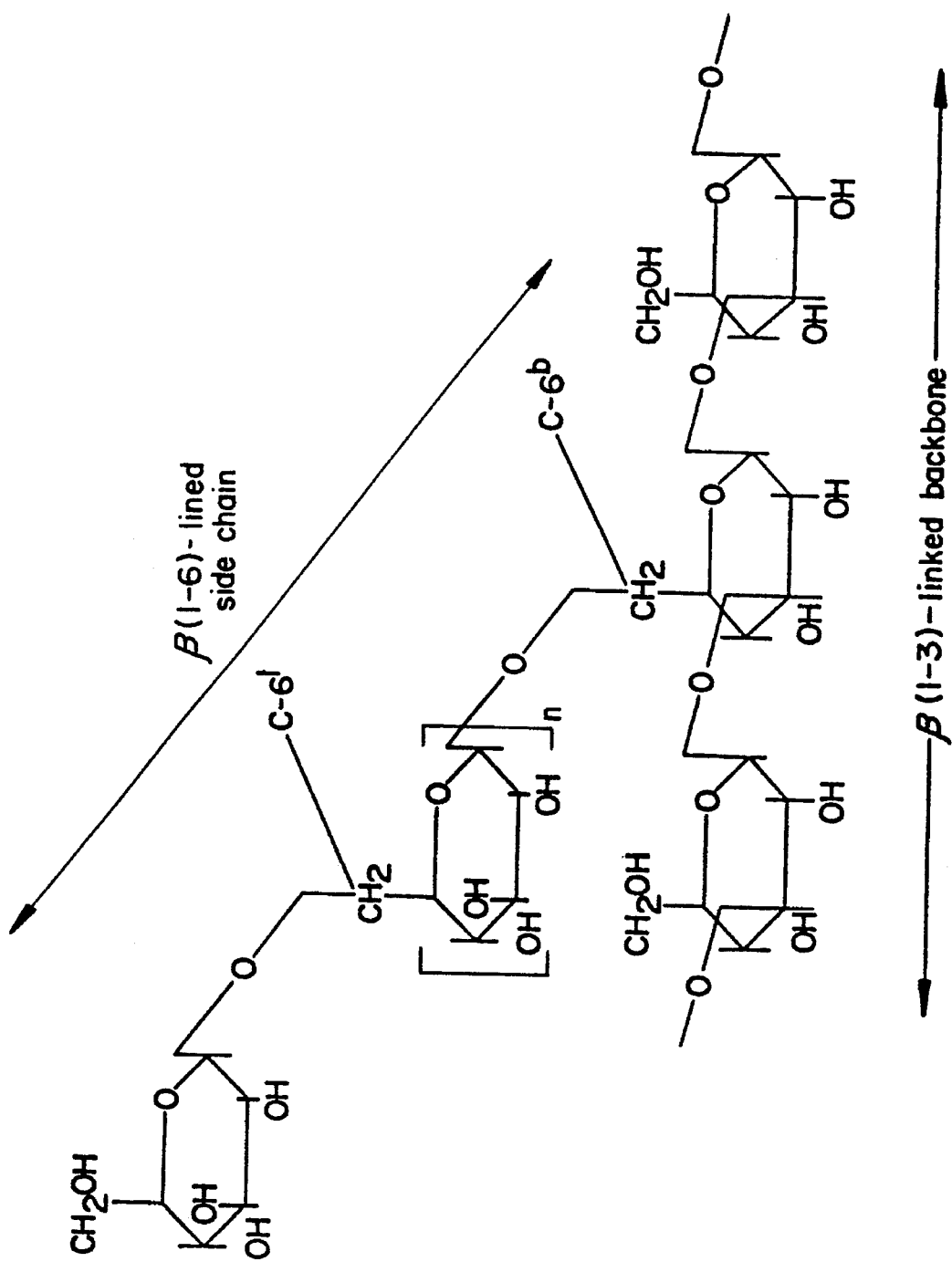
FIG. 4 is a schematic illustration of a modified glucan molecule showing the β(1–3)-linked backbone and β(1–6)-linked side chain.

The modified glucan contains an additional distinct signal at approximately 69 ppm (white box, shown as C-$6^1$ in FIG. 4), which represents an internal β(1–6)-linked glucose moiety of the branch demonstrating branches which contain more than one glucose unit. Table 2 compares the structural parameters reported for the existing glucans to those of the modified glucans.

TABLE 2

Branching and Linkage Structure of Glucans

| Glucan | Branching Frequency[1] | Number of Glucose Units per Branch | β(1–6)/β(1–3) Linkage Ratio |
|---|---|---|---|
| Curdlan | 0 | 0 | 0 |
| Soluble Phosphorylated Glucan | 0 | 0 | 0 |
| Alkali-Insoluble Yeast Glucan[2] | 0.03 (1/33) | 1 | 0.03 |
| Scleroglucan | 0.33 (1/3) | 1 | 0.33 |
| Schizophyllan | 0.33 (1/3) | 1 | 0.33 |
| Lentinan | 0.40 (2/5) | 1 | 0.40 |
| Modified Glucan[3] | 0.50 (1/2) | 2 | 1.00 |

[1]Branching Frequency = number of branches/number of glucose moieties per repeating unit.
[2]Manners et al., Biochemical Journal, 135:19–36 25 (1973).
[3]Prepared from S. cerevisiae R4, Jamas et al. U.S. Pat. No. 5,028,703.

The modified glucans of this invention which exhibit improved immunologic activity are therefore characterized as having an increased β(1–6)/β(1–3) linkage ratio over existing, reported, naturally-occurring glucans, and branches which contain one or more glucose units.

Modified glucans useful in the present method are modified glucans prepared as described by Jamas et al. in U.S. Pat. Nos. 4,810,646, 5,028,703, 4,992,540, 5,082,936 and in S. Jamas et al., Biotechnology and Bioengineering, 28:769–784 (1986); the teachings of all of which are hereby incorporated herein by reference. As shown in Table 2, modified glucans have a β(1–6)/β(1–3) linkage ratio and a branch frequency greater than 0.40.

Modified β-glucans from any strain of yeast can be used, however S. cerevisiae is the preferred strain. Modified β-glucan may be produced, for example, from other strains of yeast, including Saccharomyces delbrueckii, Saccharomyces rosei, Saccharomyces microellipsodes, Saccharomyces carlsbergensis, Schizosaccharomyces pombe, Kluyveromyces lactis, Kluyveromyces fragilis, Kluyveromyces polysporus, Canadia albicans, Candida cloacae, Candida tropicalis, Candida utilis, Hansenula wingei, Hansenula arni, Hansenula henricii and Hansenula americana.

Modified β-glucans which are particularly useful in the present method are the highly branched β-glucans derived from a mutant strain of yeast, Saccharomyces cerevisiae R4, (NRRL Y-15903), described by Jamas, et al., Biotechnology and Bioengineering, 28:769–784 (1986), and in U.S. Pat. No. 5,028,703. These modified glucans have enhanced in vitro and in vivo macrophage-activating properties when compared to naturally-occuring and commercial glucan preparations. More specifically, it has been found that macrophage activating properties are related to the degree and type of β(1–6) branching present on the glucan molecule. The modified glucans derived from the mutant yeast strain, S. cerevisiae R4, for example, have significantly more β(1–6) branching than wild-type β-glucans, as shown in Table 2, and potentiate a stronger, more pronounced immune response than wild-type and non-modified glucan preparations.

The terms "naturally occuring glucans" and "wild-type glucans" are meant to include glucans and glucan preparations in which the glucan polymer itself or the organism which produces it (e.g., bacteria, yeast cells) has not been treated or modified to change the structure of the glucan, particularly the ratio of β(1–6)/β(1–3) linkages. Naturally occuring and wild-type glucans include previously reported commercial preparations such as, e.g., Zymosan, Lentinan and Glucan-P.

The specific activity or potency of a particular glucan preparation will depend primarily on its ability to be recognized and bound to the monocyte β-glucan receptors. The β(1–6) enriched modified glucans exhibit an increased affinity for the glucan receptors of human monocytes and neutrophils. This increased biologic activity of the modified glucans is preserved regardless of the method of preparation or the state of the polymer i.e., particulate or soluble.

As used herein, it should be understood that the terms "modified β-glucan" and "modified glucan" are intended to include biologically acceptable analogs of the present modified β-glucans. The term "analogs" includes chemically related structures which have the same biological effects as modified β-glucan.

This invention is specifically directed to a method of stimulating the immune system in an individual (animal or human) by the oral or parenteral administration of compositions containing modified β-glucan or derivatives thereof. The present method is effective in boosting the immune response, for example, of individuals, or patients, who are injured, immunocompromised or protein malnourished. An immunocompromised individual is generally defined as a person who exhibits an attenuated or reduced ability to mount a normal cellular or humoral defense to challenge by infectious agents, e.g., viruses, bacteria, fungi and protozoa. A protein malnourished individual is generally defined as a person who has a serum albumin level of less than about 3.2 grams per deciliter (g/dl) and/or unintentional weight loss of greater than 10% of usual body weight.

More particularly, the method of the invention can be used to therapeutically or prophylactically treat animals or humans who are at a heightened risk of infection due to imminent surgery, injury, illness, radiation or chemotherapy, or other condition which deleteriously affects the immune system. The method is useful to treat patients who have a disease or disorder which causes the normal metabolic immune response to be reduced or depressed, such as HIV infection (AIDS). For example, the method can be used to pre-initiate the metabolic immune response in patients who are undergoing chemotherapy or radiation therapy, or who are at a heightened risk for developing secondary infections or post-operative complications because of a disease, disorder or treatment resulting in a reduced ability to mobilize the body's normal metabolic responses to infection. Treatment with the modified glucan preparations has been shown to be particularly effective in mobilizing the host's normal immune defenses, thereby engendering a measure of protection from infection in the treated host.

In the present method, modified glucans are administered to a patient, resulting in the amplification of host defenses which involve a cascade of interactions primarily mediated by macrophages and macrophage-derived products. Some of these responses which can be measured are: phagocytic activity, release of inflammatory factors (leukotrienes), release of lysozymal enzymes, release of interleukins -1,4 and 6, release of colony stimulating factors, hemopoietic proliferation, release of tumor necrosis factor (TNF) and enhanced antigen presentation.

Figure 5:
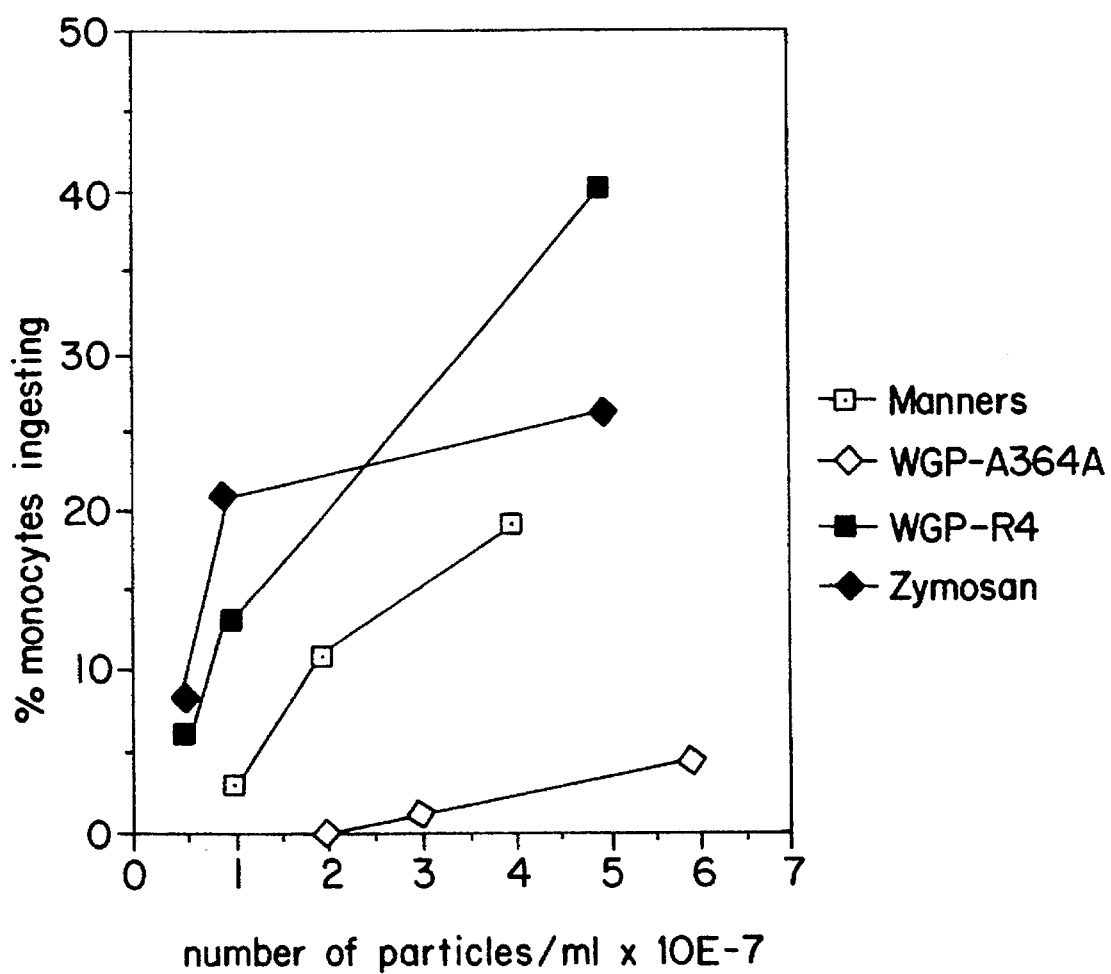
FIG. 5 is a graph comparing the levels of stimulation of phagocytic capacity in human monocytes with various glucan preparations, measured by the percentage of monocytes which ingest the glucan preparations.

In one embodiment of the present invention, modified glucan particles produced from the mutant yeast strain *S. cerevisiae* R4 were assayed for their ability to activate the above responses. These modified preparations exhibited significantly enhanced biologic activity when compared to the following glucan products: alkali-insoluble non-modified wild-type glucan prepared according to the procedure of Manners et al., *Biochem. J.*, 135:19–36 (1973), Zymosan, which is a commercial particulate preparation of yeast cell walls (Sigma Chemical Co.), and non-modified whole glucan particles derived from *S. cerevisiae* A364A, (U.S. Pat. No. 4,810,646) the parent strain of *S. cerevisiae* R4, which has a lower ratio of $\beta(1-6)/\beta(1-3)$ linkages than the R4 preparation. The results, shown in FIG. 5, illustrate the increased efficacy of modified glucan to trigger phagocytosis in human monocytes. Enhanced phagocytosis is expressed as the precentage of monocytes ingesting three or more glucan particles per cell. Modified glucan particles from *S. cerevisiae* R4 showed enhanced stimulation of phagocytosis both in terms of total number of monocytes ingesting the glucan, and in total number of glucan particles ingested per monocyte population. The modified structure of the R4 glucan preparation, which has a significantly higher ratio of $\beta(1-6)/\beta(1-3)$ linkages than the other glucan preparations, has greater affinity for the glucan receptor giving it a higher specific activity.

Figure 6:
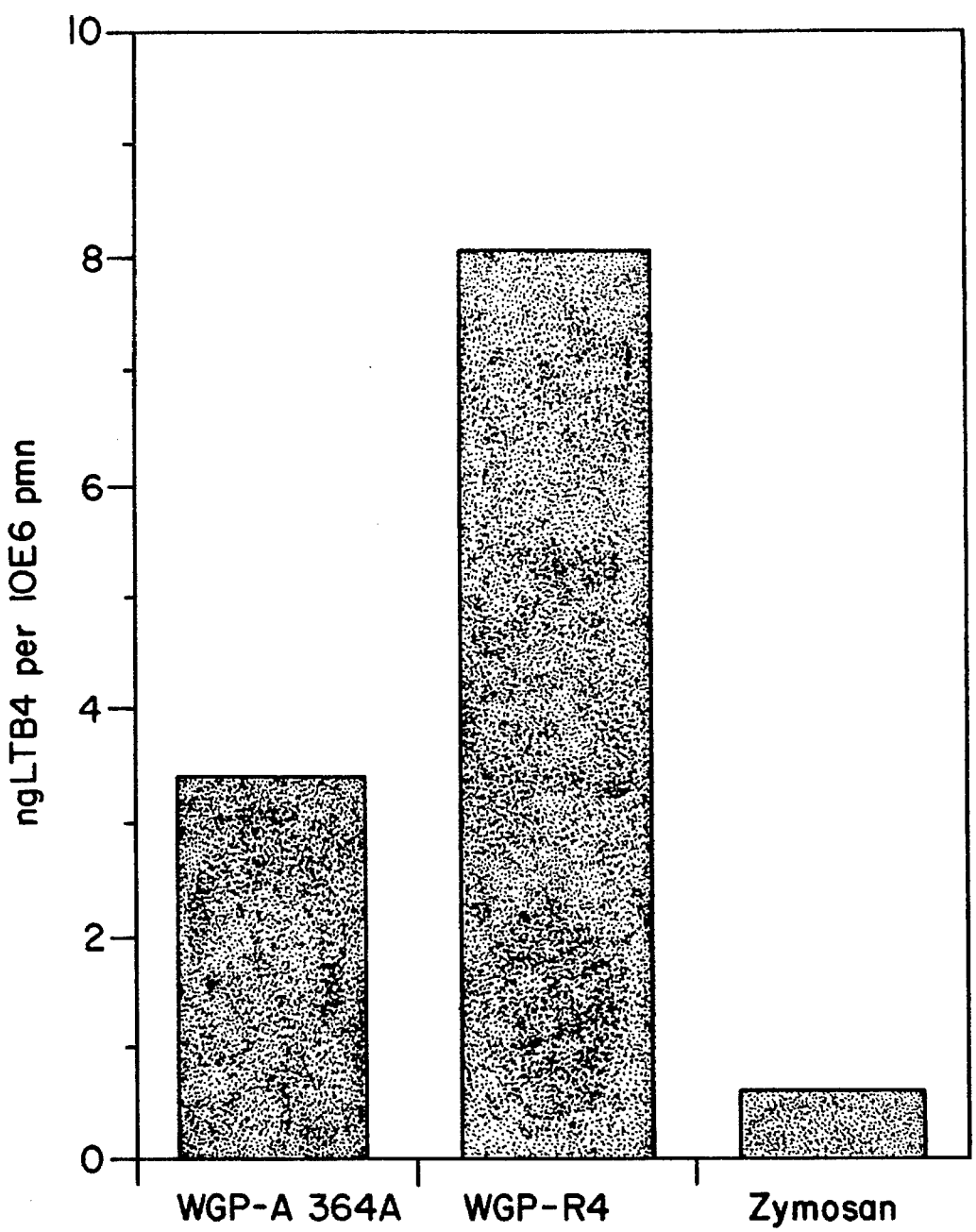
FIG. 6 is a graph showing the induction of synthesis of leukotriene $B_4$ ($LTB_4$) in human neutrophils by Zymosan, modified glucan particles derived from S. cerevisiae R4 and non-modified glucan particles derived from S. cerevisiae A364A.

In another embodiment, neutrophils were assayed for production of the inflammatory mediator, leukotriene $B_4$ (LTB$_4$) upon incubation with various glucan preparations. The modified R4 glucan preparation (WGP-R4) induced a higher level of synthesis of LTB$_4$, as shown in FIG. 6, than glucan particles derived from *S. cerevisiae* A364A (WGP-A364A), and substantially higher than Zymosan. These results show that modified glucans derived from *S. cerevisiae* R4 demonstrate an increased avidity for the glucan receptor of monocytes when compared to non-modified naturally-occurring glucans.

In another embodiment, a water-soluble preparation of R4 modified glucan was prepared by partial acid hydrolysis, using a process described by Jamas et al. in U.S. Pat. No. 5,322,841 filed concurrently herewith, the teachings of which are incorporated by reference herein. The avidity of this soluble preparation for the glucan receptor was determined by measuring its ability to competitively occupy the glucan receptor thus inhibiting the uptake of Zymosan particles. The concentration of soluble glucan required to obtain 50% inhibition of ingestion was measured. Table 3 summarizes the receptor avidity data of the solubilized modified glucan preparation and other naturally-occurring soluble glucans.

TABLE 3

Inhibition of Zymosan Ingestion in Monocytes
Avidity of Soluble Glucans for the
Monocyte Glucan Receptor

| POLYSACCHARIDE | CONC. FOR 50% INHIBITION (mg/ml) | RELATIVE AVIDITY |
|---|---|---|
| Barley β-glucan[1] | 65 | 1 |
| Laminarin (algae)[1] | 32 | 2 |
| Yeast extract glucan | 3.5 | 19 |
| Non-modified Glucan (A364A) | 1.5 | 43 |
| Modified Glucan (R4) | 0.1 | 650 |

[1]Czop and Austen, Journal of Immunology, 135:3388–3393 (1985)
[2]Janusz et al., Journal of Immunology, 137:3270–3276 (1986)

The modified glucan composition of the present invention can be administered as a preventative treatment, for example, up to 72 hours before surgery, chemotherapy, or other event which will put the patient at risk for infection. Modified glucan preparations may be administered after the event, for example, for a period of up to 96 hours for malnourished patients, or longer periods to individuals experiencing chronic immunosuppression, such as that which occurs during chemotherapy. By this treatment, the patients' non-specific and specific host defenses are stimulated by the modified β-glucan preparation to produce endogenous mediators (e.g., IL-1, TNF) which in turn mediate a series of metabolic events, including potentiating lymphocyte activity in response to antigens, macrophage activity in phagocytosis, release of colony-stimulating factors, and increased lysozyme and leukotriene production from monocytes and neutrophils. These metabolic functions are directly beneficial in fighting secondary infections associated with post-operative complications, and in boosting the suppressed immune response associated with chemotherapy, radiation therapy, kidney failure, AIDS and other disorders. Thus, an injured, immunocompromised or protein malnourished patient will be able to mount sufficient humoral and cellular defenses to better survive secondary infections.

The administration of modified β-glucan is more advantageous than the direct exogenous administration of cytokines, such as IL-1 or the colony stimulating factors, for several reasons. Cytokines are made primarily by recombinant genetic engineering techniques, are difficult and expensive to purify, and result in considerable toxicity and adverse side-effects. The administration of modified glucan preparations stimulates the endogenous release of the various cellular mediators in balanced proportions.

The compositions administered in the method of the present invention can optionally include, in addition to modified β-glucan, other components. The other components included in a particular composition are determined primarily by the manner in which the composition is to be administered. For example, a composition to be administered orally in tablet form can include, in addition to modified β-glucan, a filler (e.g., lactose), a binder (e.g., carboxymethyl cellulose, gum arabic, gelatin), an adjuvant, a flavoring agent, a coloring agent and a coating material (e.g., wax or plasticizer). A composition to be administered in liquid form can include whole β-glucan and, optionally, an emulsifying agent, a flavoring agent and/or a coloring agent. A composition for parenteral administration can be mixed, dissolved or emulsified in water, sterile saline, PBS, dextrose or other biologically acceptable carrier.

The mode of administration of the modified glucan preparation can be oral, enteral, parenteral, intravenous, subcutaneous, intraperitoneal, intramuscular, topical or intranasal. The form in which the composition will be administered (e.g., powder, tablet, capsule, solution, emulsion) will depend on the route by which it is administered. The quantity of the composition to be administered will be determined on an individual basis, and will be based at least in part on consideration of the severity of infection or injury in the patient, the patient's condition or overall health, the patient's weight and the time available before surgery, chemotherapy or other high-risk treatment. In general, a single dose will preferably contain approximately 0.001 to approximately 200.00 mg of modified glucan per kilogram of body weight.

In general, the compositions of the present invention can be administered to an individual periodically as necessary to stimulate the individual's immune response. An individual skilled in the medical arts will be able to determine the length of time during which the composition is administered and the dosage, depending on the physical condition of the patient and the disease or disorder being treated. As stated above, the composition may also be used as a preventative treatment to pre-initiate the normal metabolic defenses which the body mobilizes against infections.

The present method, utilizing modified glucans which provide a heightened immune response, is particularly effective for therapeutically or prophylactically mobilizing an individual's immune system.

The invention is further illustrated by the following examples, which are not to be taken as limiting in any way.

EXAMPLES

Example 1

Activation of Phagocytosis by Human Monocytes

The following glucan preparations were tested for their capacity to trigger phagocytosis in human monocytes:

(1) Zymosan (Sigma Chemical Company, St. Louis, Mo.) —a commercial yeast cell wall preparation.

(2) Alkali-insoluble glucan—prepared from Baker's yeast according to the procedure of Manner's et al., *Biochem J.*, 135:19–30 (1973).

(3) WGP-A364A—Whole glucan particles prepared from *Saccharomyces cerevisiae* A364A according to the method described by Jamas et al. in U.S. Pat. No. 4,810,646.

(4) WGP-R4—Whole glucan particles prepared from *Saccharomyces cerevisiae* R4 (U.S. Pat. Nos. 4,810,646 and 5,028,703.

The preparations were incubated at 37° C. with adherent human monocytes at glucan particle concentrations of $5 \times 10^6$/ml to $6 \times 10^7$/ml (0.01 mg/ml to 0.3 mg/ml) corresponding to particle-to-cell ratios of approximately 5 to 50, respectively. The number of glucan particles ingested by at least 300 monocytes was determined by direct visual observation with a 1000X light microscope. The results, shown in FIG. 5, are expressed as the percentage of monocytes ingesting three or more ($\geq 3$) glucan particles per cell. Whole glucan particles from the mutant strain R4 (WPG-R4) exhibited enhanced stimulation of phagocytosis both in terms of total number of monocytes ingesting and in total number of particles ingested per monocyte population.

Example 2

Enhanced Stimulation of Macrophage Secretory Activity with Modified Glucans

Human neutrophils were assayed for production of the inflammatory mediator, leukotriene $B_4$ ($LTB_4$) upon incubation for 45 minutes at 37° C. with 3 mg/ml hexose equivalents of glucan preparations. The determination of $LTB_4$ production was measured by radioimmunoassay (RIA) according to the procedure of Czop and Austen. Czop and Austen, *Proc. Nat'l. Acad. Sci.*, 82:2751–2755 (1985). The modified glucan, WGP-R4, induced considerably higher levels of $LTB_4$ than any of the other glucan preparations tested. The results are shown in FIG. 6.

Human monocytes were assayed for expression of tumor necrosis factor (TNF) upon activation with the glucan preparation, WGP-R4, and Glucan-P (Accurate Chemical and Scientific Corporation, Westbury, Conn.) a particulate preparation from Baker's yeast. Human monocytes isolated from purified mononuclear cell preparations were incubated with 5, 15 and 50 μg/ml of the glucan preparations. Monocyte supernates and cells were freeze-thawed three times, sonicated and assayed for TNF using a murine L-M connective tissue and cell cytotoxicity bioassay as described by Miller-Graziano, *In: The Immune Consequences of Trauma, Shock and Sepsis*. The results shown in FIG. 7 are for total TNF produced (i.e., secreted TNF and cell-associated TNF).

Figure 7:
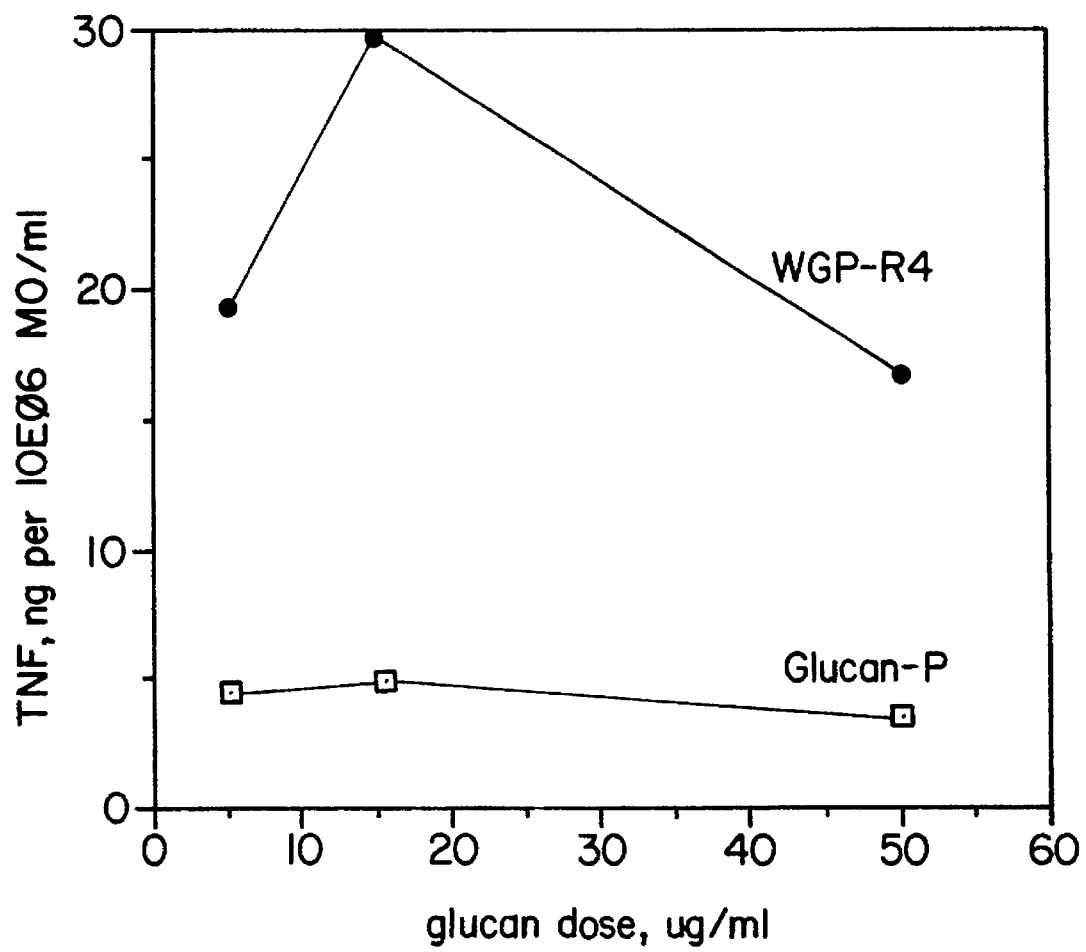
FIG. 7 is a graph showing induction of TNF in human monocytes by modified glucan particles derived from S. cerevisiae R4, and by Glucan-P.

As shown in FIG. 7, the modified glucans, WGP-R4, exhibit a greatly enhanced ability to activate monocytes as measured by TNF production.

Example 3

Affinity of Modified Glucans for the Monotype β-glucan Receptor

The ability of glucan molecules to be recognized and bound to the β-glucan receptor of monocytes is critical for their biological activity. Modified glucans derived from the mutant strain R4 (WGP-R4) demonstrated an increased affinity for the glucan receptor of monocytes when compare to naturally occurring glucans from Baker's yeast. Janusz et al., *J. of Immunol.*, 137:3270–3276 (1986).

A water soluble modified glucan preparation of WGP-R4 was prepared using a process described by Jamas et al. in co-pending application Ser. No. 07/404,737, filed concurrently herewith, and incorporated by reference herein. Human monocytes were incubated with various concentrations of soluble glucans for 15 minutes, washed to remove unbound glucan and then incubated with Zymosan for 30 minutes. After fixing and staining the monolayers, the percentage of monocytes ingesting Zymosan was determined. The affinity of glucan preparations for the β-glucan receptor by was measured according to their ability to competitively occupy the receptor thus inhibiting the uptake of Zymosan by monocytes. Samples were compared by taking the concentration of glucan required to obtain 50% inhibition of Zymosan ingestion.

Figure 8:
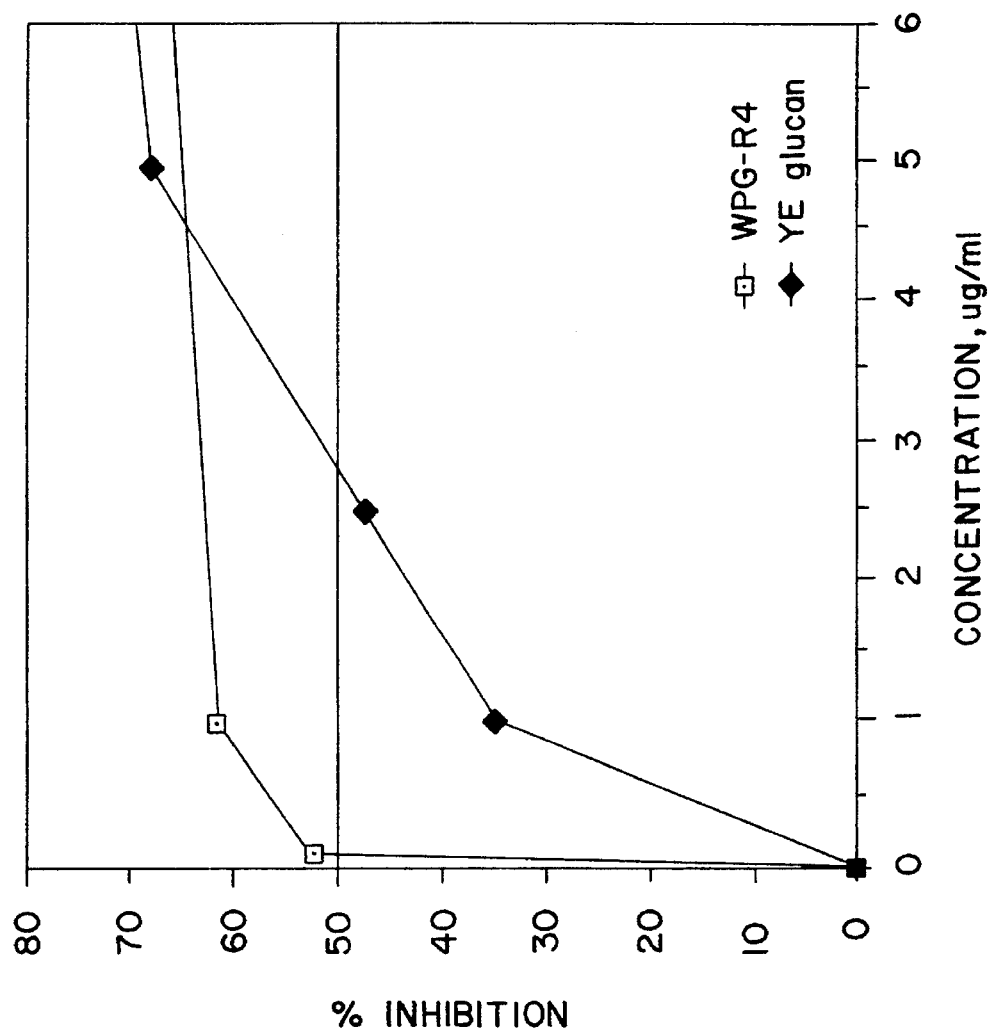
FIG. 8 is a graph showing the dose-dependent inhibitory effect on monocyte ingestion of Zymosan by modified glucan derived from S. cerevisiae R4 and yeast extract (YE) glucan.

The significantly enhanced affinity of the modified glucan WGP-R4, to the receptor is evident by the low concentration required to obtain a 50% inhibition of Zymosan ingestion. The results presented in FIG. 8 demonstrate that the modified glucan, WGP-R4, binds to the monocyte β-glucan receptor with a much higher affinity (0.1 μg/ml) than soluble glucan from Baker's yeast extract (3.5 μg/ml), (YE glucan) representing a 35-fold increase in activity.

Example 4

In Vivo Activity of Modified Glucans

The effect of in vivo administration of modified glucans on peripheral white blood cell (WBC) counts was characterized in mice. Soluble preparations of the modified glucan from strain R4 were administered intravenously (IV) and subcutaneously (SC) to male CD-1 mice and total and differential cell counts were monitored at regular time intervals.

Figure 9:
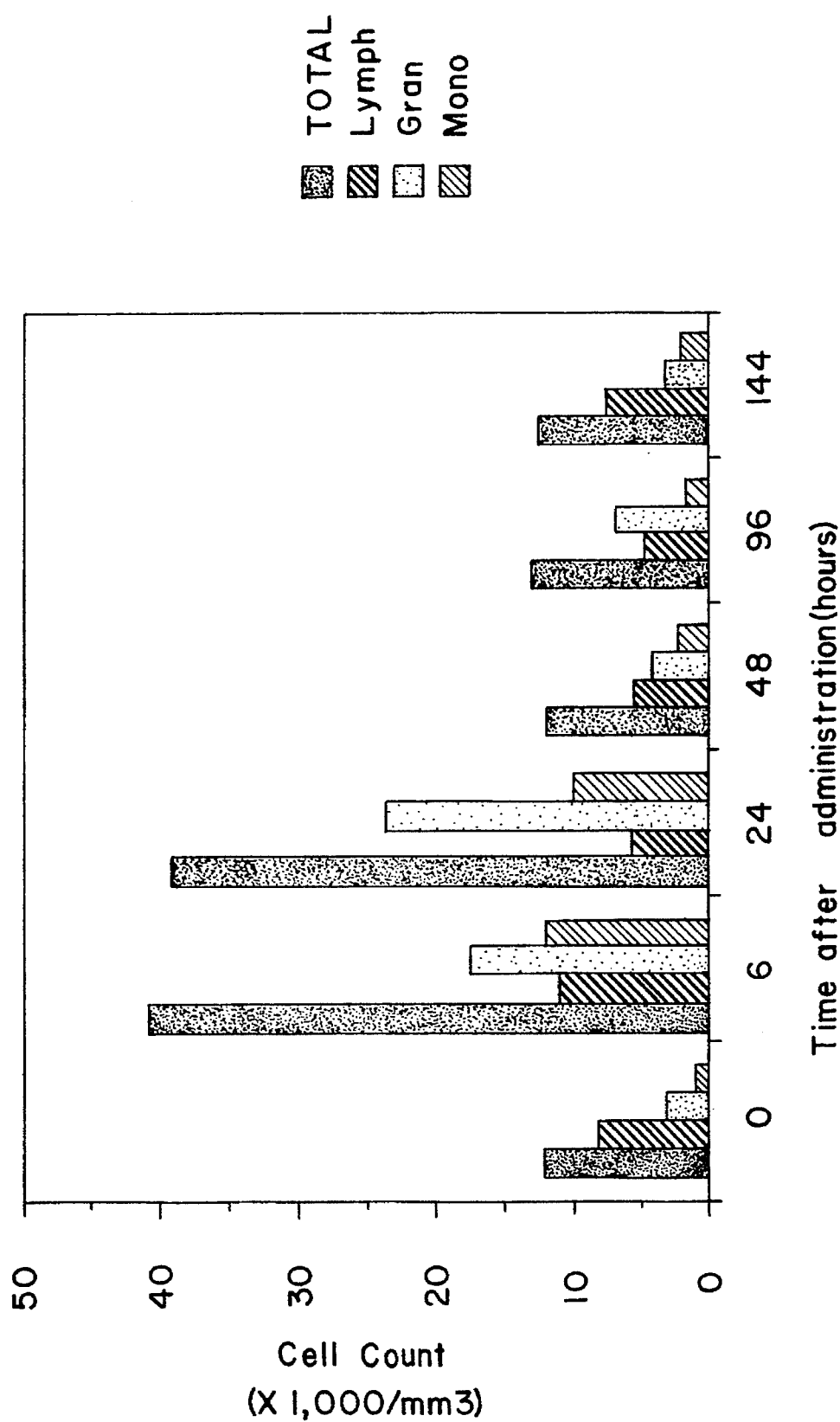
FIG. 9 is a graph showing the change in peripheral total and differential white blood cell counts in mice after a single, intravenous dose of modified glucan (5 mg/mouse).
Figure 10:
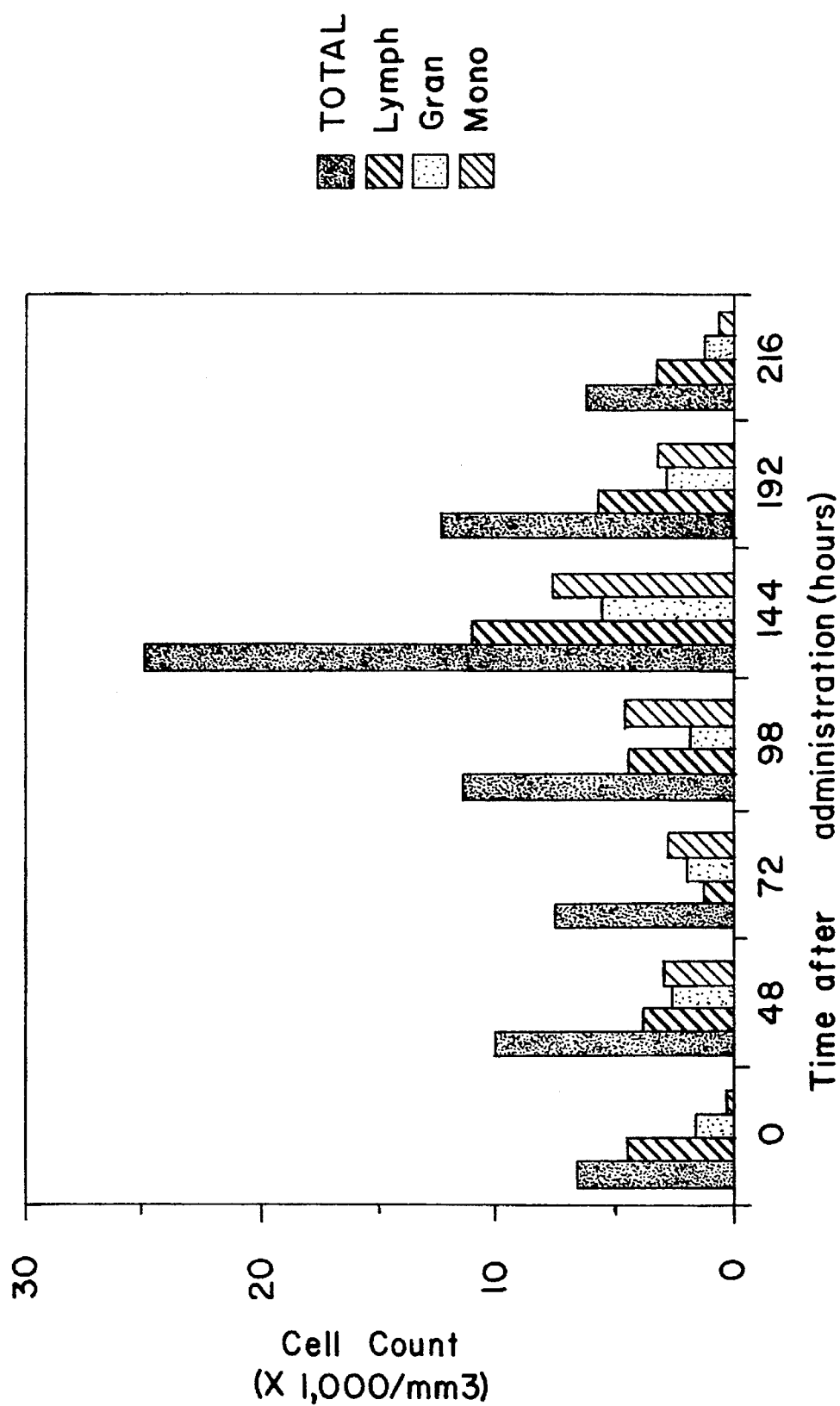
FIG. 10 is a graph showing peripheral, total and differential white blood cell counts in mice after multiple-dose sub-cutaneous administration of modified glucan (5 mg/mouse/day×4 days).

A profound increase in the total WBC count was observed particularly following single-dose IV administration. FIGS. 9 and 10 summarize the results, which show rapid (<6 hours) amplification of total WBC counts with, the most pronounced increase (12X and 6X) occurring in the monocyte and granulocyte counts, respectively. This is consistent with in vitro data suggesting the presence of a high affinity β-glucan receptor present on human monocytes. The multiple-dose SC regimen (FIG. 10) elicited an increase in total WBC beginning at 48 hours and peaking at 144 hours after initiation of therapy. The increase in total counts was consistent with an increase in the peripheral monocyte population over this time period. The average monocyte count increased from $320/mm^3$ at zero hours to approximately $8,000/mm^3$ at 144 hours, representing at 24-fold increase.

Example 5

Infection Model

A sepsis model was developed in mice to characterize the efficacy of modified glucans in protecting an immunologically intact host against serious infections, such as those which commonly occur following abdominal surgery.

Figure 11:
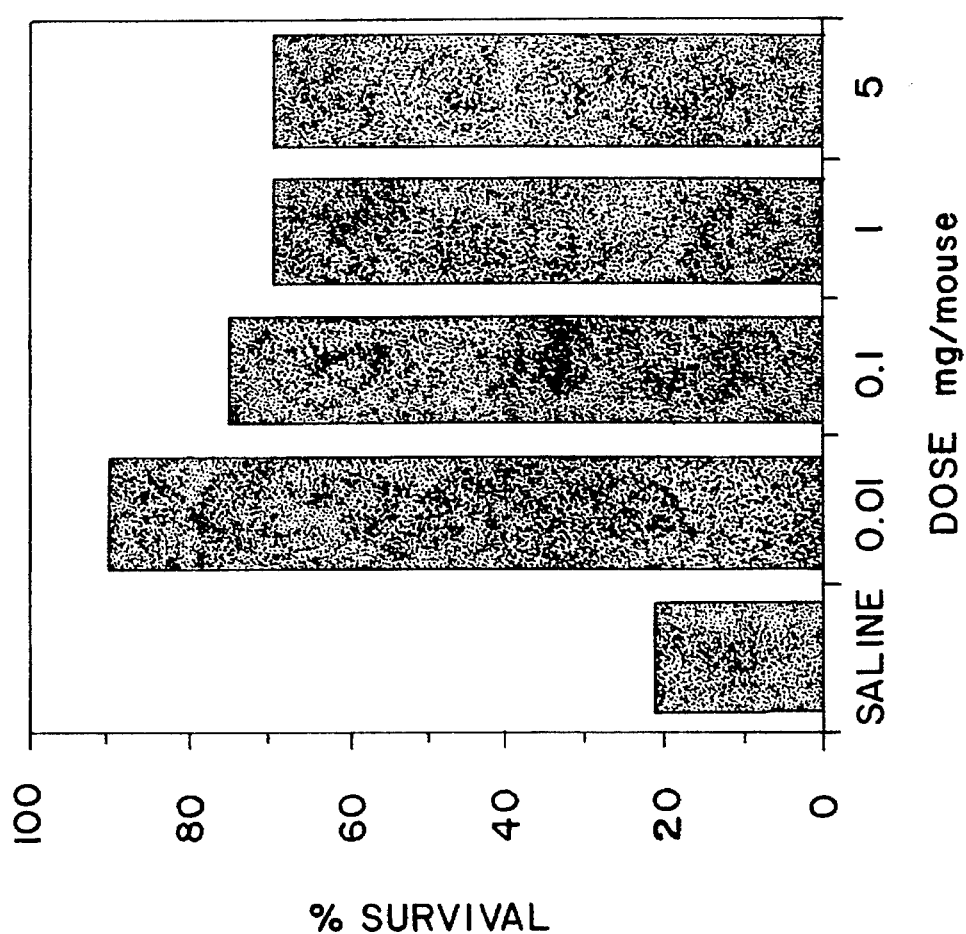
FIG. 11 is a graph showing the efficacy of the modified glucans in an E. coli sepsis model in mice.

The model used intraperitoneal challenge of mice with an 0.1 ml suspension of *E. coli* strain TVDL-rat (approximately $10^8$ CFU/ml) 24 hours following IV administration of modified glucan, by single bolus injection using transthoracic cardiac puncture. Mice were returned to their cages and maintained on food and water ad libitum. A control group of 10 mice were injected with 0.1 ml sterile saline at the time of the modified glucan administration. Mortality rates for the treatment groups and saline control group were recorded at 48 hours after challenge. The results, shown in FIG. 11, demonstrated that modified glucans significantly reduced mortality, as compared to the saline control group (p<0.05) at doses as low as 0.01 mg/mouse (0.5 mg/kg body weight).

Example 6

Enhanced Hemopoietic Effects of Modified Glucans

Figure 12:
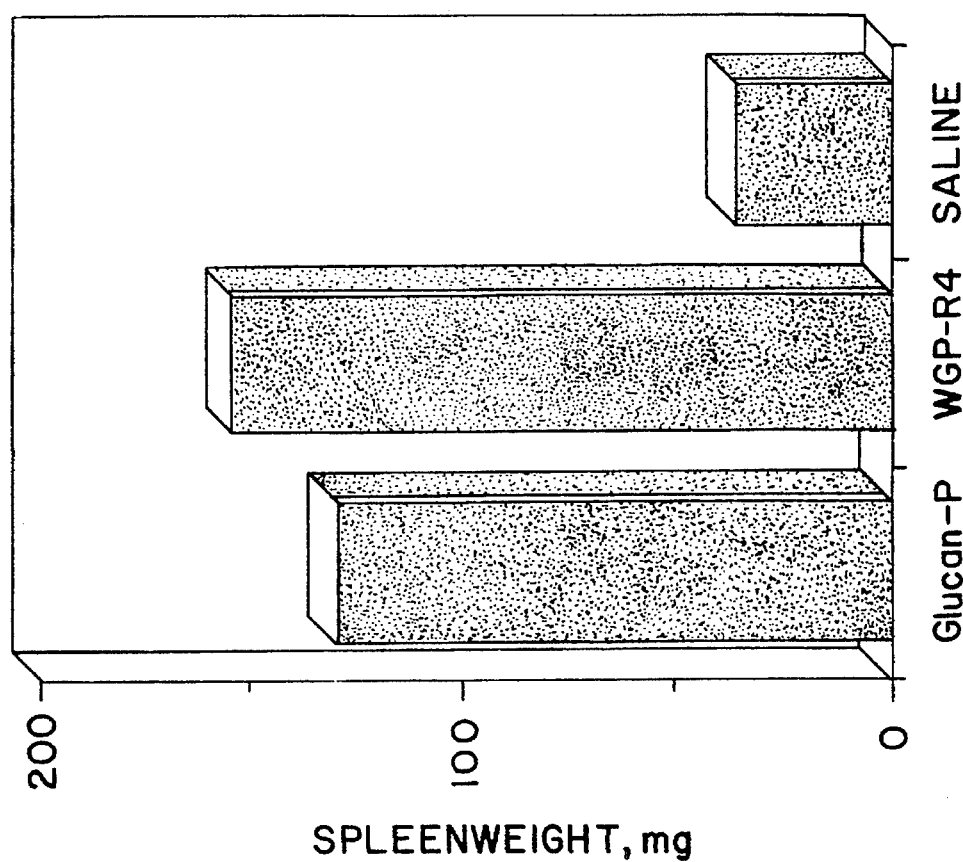
FIG. 12 is a graph comparing the effect of modified glucan derived from S. cerevisiae R4 and Glucan-P on hemopoietic proliferation in mice exposed to 6.75 Gy $^{60}$Co irradiation.
Figure 13:
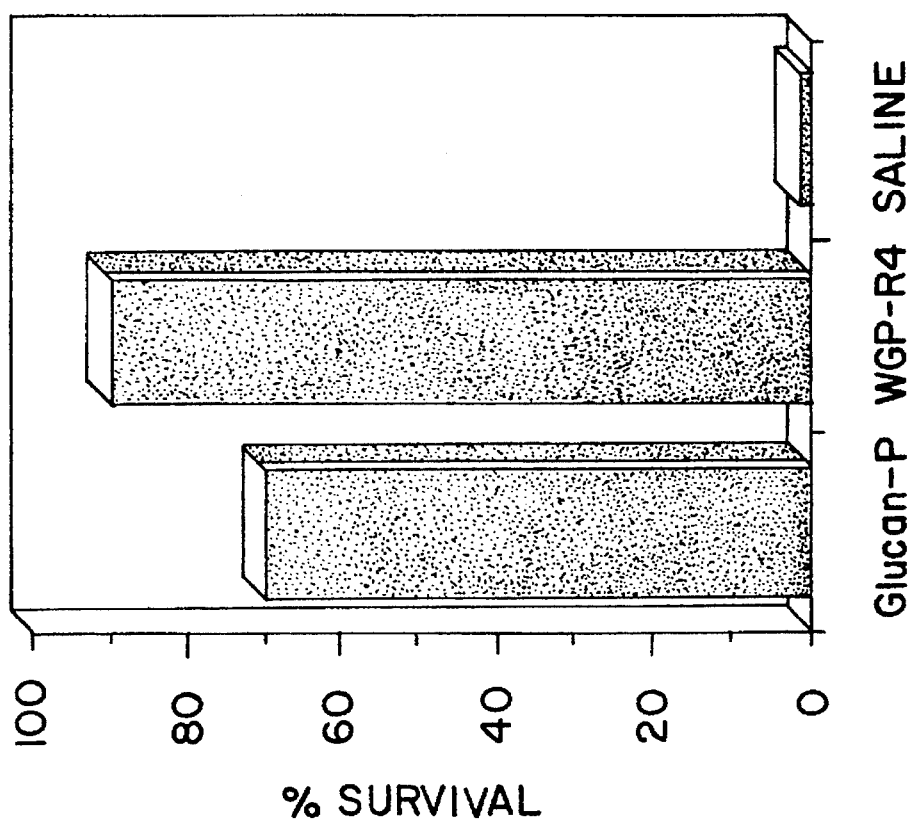
FIG. 13 is a graph showing the effect of modified glucan administration on the 30-day survival rate of mice exposed to 8.25 Gy $^{60}$Co irradiation.

Glucan particles produced from *Saccharomyces cerevisiae* R4 (WGP-R4) and Glucan-P (Accurate Chemical and Scientific Corporation) were administered as a single IV dose (5 mg) to mice, 24 hours before a potentially lethal radiation exposure. Under these conditions, mice receiving the control saline died of infectious complications arising from radiation-induced myelosuppression. The effect of the glucans on stimulating hemopoietic proliferation and recovery was reflected in the increase of average spleen weights. FIG. 12 demonstrates the higher stimulation effected by modified glucans. This effect is substantiated by the 30 day survival data which is presented in FIG. 13, which shows that the group receiving the modified glucan (WGP-R4) had a 90% survival rate compared to 70% survival for the Glucan-P group.

Figure 14:
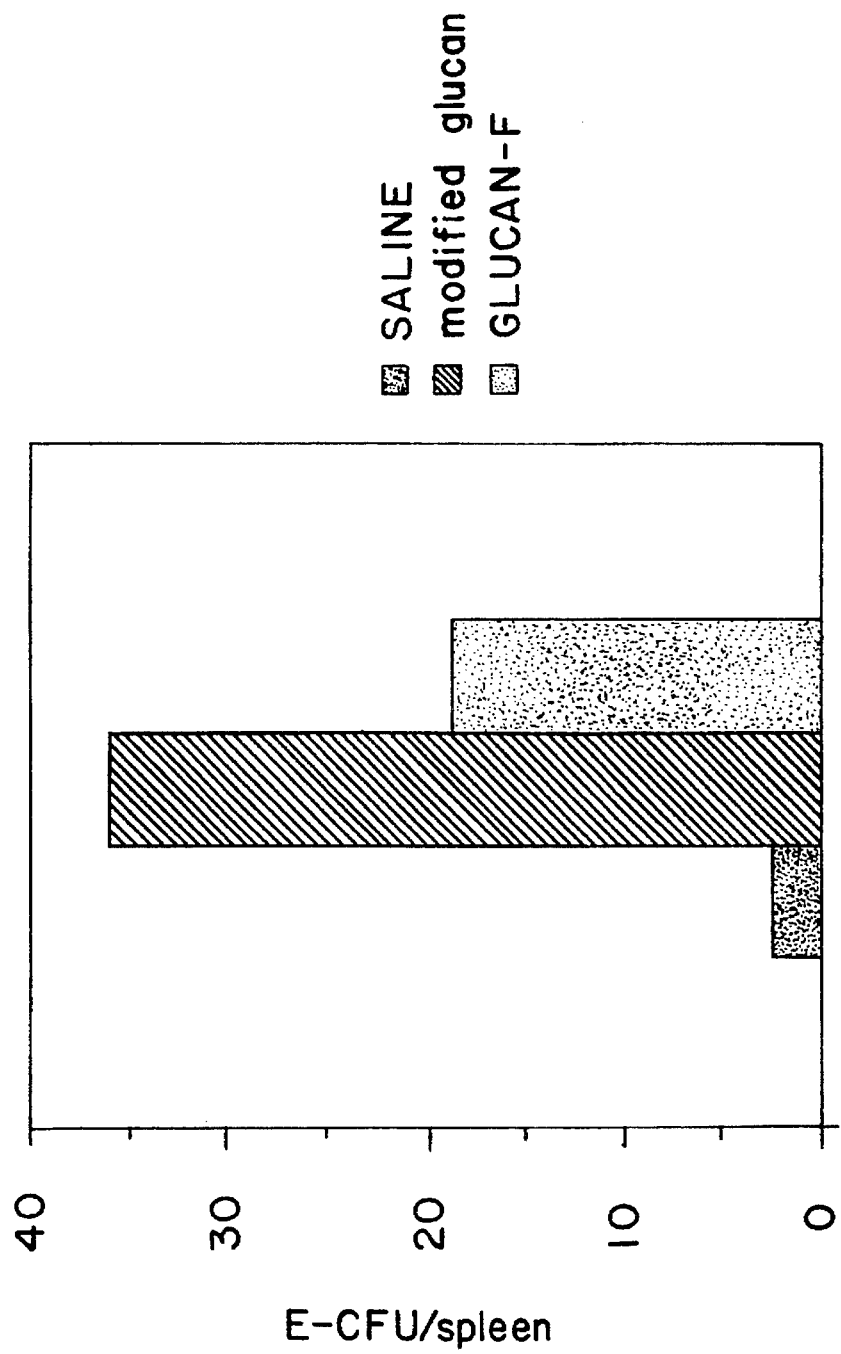
FIG. 14 is a graph showing the effect of a single dose of modified glucan or Glucan-F on stimulating endogenous spleen colony-forming units (E-CFU) in mice exposed to 6.75 Gy $^{60}$Co irradiation.

The enhanced stimulatory activity of the modified glucans from strain R4 was also observed with soluble preparations of the modified glucans. Solubilized modified glucans from strain R4 were administered to mice by single IV injection (5 mg/mouse) before exposure to $^{60}Co$ irradiation. The stimulation and recovery of hemopoietic stem cells was measured by counting the endogenous spleen (colony-forming units (E-CFU). As shown in FIG. 14 the modified soluble glucan resulted in significantly higher levels of hemopoietic cell proliferation when compared to the previously reported (Patchen and MacViltie, *J. Biol. Resp. Mod.*, 1986) soluble preparation, Glucan-F from Baker's yeast.

Equivalents

Those skilled in the art will recognize or be able to ascertain, using no more than routine experimentation, many equivalents to the specific materials and components described herein. Such equivalents are intended to be encompassed in the scope of the following claims.

We claim:

1. A method for inducing an immune system response in an animal comprising administering to the animal an aqueous insoluble β(1–3) glucan obtained from *Saccharomyces cerevisiae strain R4 (NRRL Y-15903)* in an amount sufficient to induce an immune system response in the animal.

2. The method of claim 1 wherein the β(1–3) glucan is administered orally or parenterally.

3. A method for treating infection in an animal comprising administering to the animal an aqueous insoluble β(1–3) glucan obtained from *Saccharomyces cerevisiae* strain R4 (NRRL Y-15903) in an amount sufficient to treat the infection in the animal.

4. The method of claim 3 wherein the β(1–3) glucan is administered orally or parenterally.

5. A method for enhancing the microbicidal activity of phagocytic cells in an animal comprising administering to the animal an aqueous insoluble β(1–3) glucan obtained from *Saccharomyces cerevisiae* strain R4 (NRRL Y-15903) in an amount sufficient for enhancing the microbicidal activity of said phagocytic cells.

6. The method of claim 5 wherein the β(1–3) glucan is administered orally or parenterally.

* * * * *